United States Patent [19]

Giddings

[11] 4,147,621

[45] Apr. 3, 1979

[54] METHOD AND APPARATUS FOR FLOW FIELD-FLOW FRACTIONATION

[75] Inventor: John C. Giddings, Salt Lake City, Utah

[73] Assignee: University of Utah, Salt Lake City, Utah

[21] Appl. No.: 810,835

[22] Filed: Jun. 28, 1977

[51] Int. Cl.² .......................... B01D 13/00; B01D 3/00
[52] U.S. Cl. ................................. 210/22 C; 210/23 F; 210/101; 210/143; 210/321 R; 210/321 B
[58] Field of Search ...................... 210/22, 23 R, 23 H, 210/23 F, 321 R, 321 B, 72, 198 C, 97, 101, 143

[56] References Cited

U.S. PATENT DOCUMENTS

| | | | |
|---|---|---|---|
| 3,449,938 | 6/1969 | Giddings | 210/72 X |
| 3,835,040 | 9/1974 | Mahlman et al. | 210/23 F X |
| 3,891,547 | 6/1975 | Chang et al. | 210/321 R X |
| 4,075,092 | 2/1978 | White et al. | 210/22 R |

OTHER PUBLICATIONS

Theoretical & Exper. Characterization of F–FFF, Giddings et al., Analytical Chemistry, vol. 48, #8, 7/76, pp. 1126–1132.

F–FFF: New Method for Separating...Viruses, Giddings et al., Journal of Virology, Jan. 1972, pp. 131–138.

*Primary Examiner*—Ferris H. Lander
*Attorney, Agent, or Firm*—Criddle, Thorpe and Western

[57] ABSTRACT

A method and apparatus for flow field-flow fractionation involving the application of a lateral cross flow superimposed on a channel fluid flow in a field-flow fractionation system. The cross flow is developed by applying a pressure across semipermeable plates which substantially define a narrow channel region carrying a fluid substance to be subjected to the influence of the cross flow. This cross flow causes differential migration of solute material carried by the channel flow, thereby providing application to numerous processes such as separations, fractionation, solute exchange, purification, dialysis and ultrafiltration.

13 Claims, 7 Drawing Figures

METHOD AND APPARATUS FOR FLOW FIELD-FLOW FRACTIONATION

This invention was funded in part by a contract from the National Institute of Health, Department of Health, Eduction and Welfare.

BACKGROUND OF THE INVENTION

The subject of the present invention relates to a method of field-flow fractionation (FFF), and more particularly to the development of pressure-gradient fields for influencing material within such FFF systems.

FFF, disclosed previously in U.S. Pat. No. 3,449,938, is the descriptive term referring to a broad field of technology developed primarily for separation and characterization of macromolecules and particles. The technique has demonstrated a capability of dealing with an enormous mass range, including particle sizes varying from a molecular weight of 600 up to particles of 1 micrometer in diameter, a mass range of approximately $10^9$.

FFF takes advantage of the nature of viscous flow in narrow channels. Under laminar flow conditions, the velocity of flow approaches zero near the wall of the channel. Any solute or particle confined in this quiescent region near the wall will have its motion retarded relative to solutes distributed over the more active regions of the total flow cross section.

FFF employs an influencing field to partition the desired solutes into the quiescent wall regions of a narrow column. The field is applied along an axis perpendicular to the flow axis. As the strength of the field is increased, the solute is driven further and further toward the wall and its downstream motion is increasingly retarded. Different solutes will be retarded differentially because they will interact to a different degree with the field and/or they will exhibit a different level of diffusivity that will selectively oppose the induced drift toward the channel wall.

Subtechniques of FFF are characterized according to the kind of field employed. Many possibilities exist, including thermal gradients, electrical fields, and sedimentation fields developed by centrifugal forces. The rate of migration of solutes in such FFF systems depends on the magnitude and type of field, the channel dimensions, the solute-field interaction, and the solute-solvent diffusion coefficient.

Some disadvantages are inherent, however, in the conventional FFF system. In each case, the force field imposed on the channel flow is external and requires particular responsive characteristics inherent within the interacting particle. Obviously, electrically neutral particles will experience negligible influence under an electric field gradient. Furthermore, different particles will respond differently, or sometimes not at all, to heat, electrical or other forces.

Other limitations arise by reason of the single inlet/outlet flow channel. Such configuration restricts the apparatus to segregation applications of various solute types within the channel fluid, as described in the referenced Patent. Such arrangement precludes solvent exchange and controlled solute concentration and dilution.

OBJECTS AND SUMMARY OF THE INVENTION

It is an object of the present invention to provide a FFF system which utilizes a cross flow as the segregating field or influence.

It is a further object of the subject invention to provide specific applications of the aforementioned apparatus, including separations, fractionation, solvent and solute exchange, filtration, dialysis, pressure dialysis, purification and experimental parameter determinations.

These objects are realized in an apparatus and method entitled flow field-flow fractionation (Flow-FFF) in which a narrow channel is formed between two closely spaced, elongated, semipermeable plate means. The channel between these plates is laterally enclosed by nonporous side wall structure, with inlet and outlet means being located at the ends of the channel. Particles carried in a channel-flow fluid are subjected to a cross fluid flow developed by a lateral pressure gradient or by other means. This cross flow fluid consists of a second fluid that passes through the respective semipermeable plate means. Utilization of cross fluid flow as a segregating force has greater versatility and broader application than prior art FFF, due to the universal effect of cross flow on all solute species.

Other objects and features will be obvious to a person skilled in the art from the following detailed description, taken in conjunction with the drawings represented in the various figures as follows.

Figure 7:
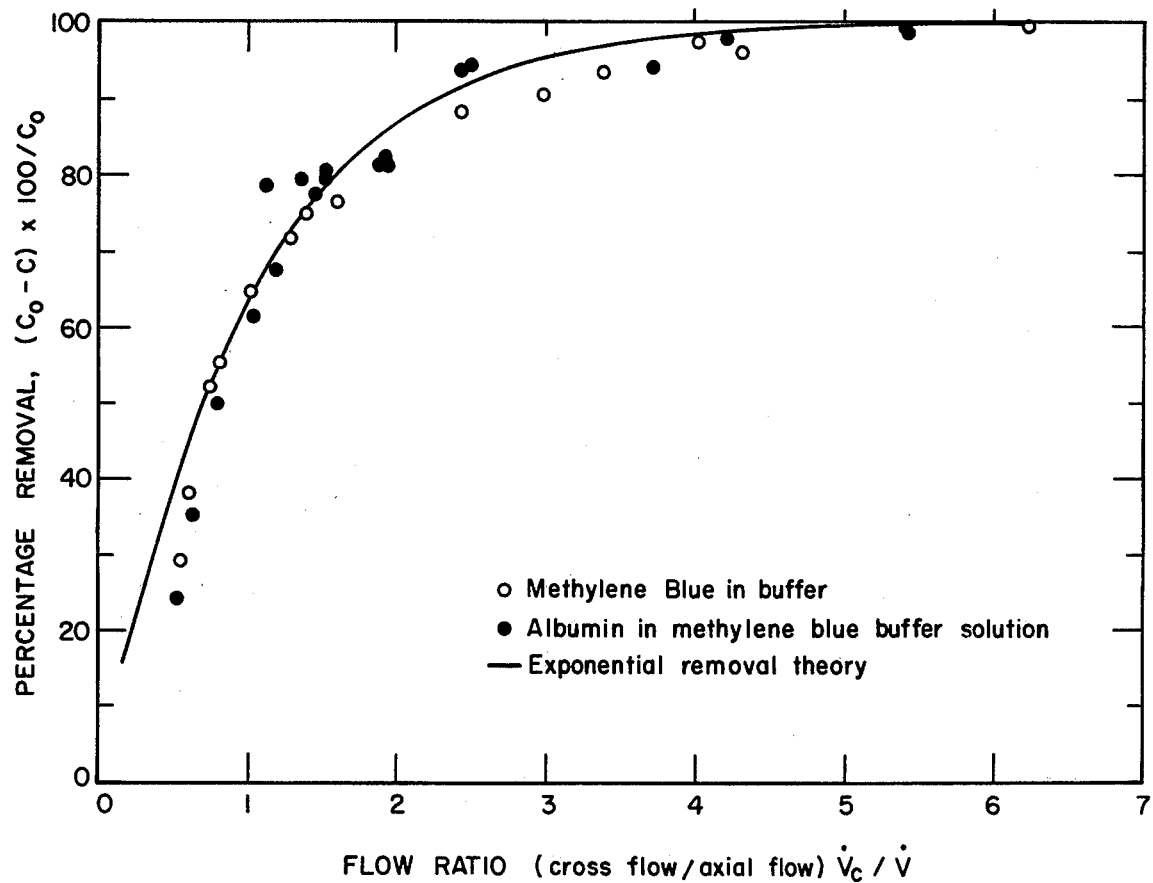

FIG. 7 graphically illustrates the effective use of Flow-FFF in separating small molecules (methylene blue) from larger molecules (albumin).

DETAILED DESCRIPTION OF THE INVENTION

Figure 1:
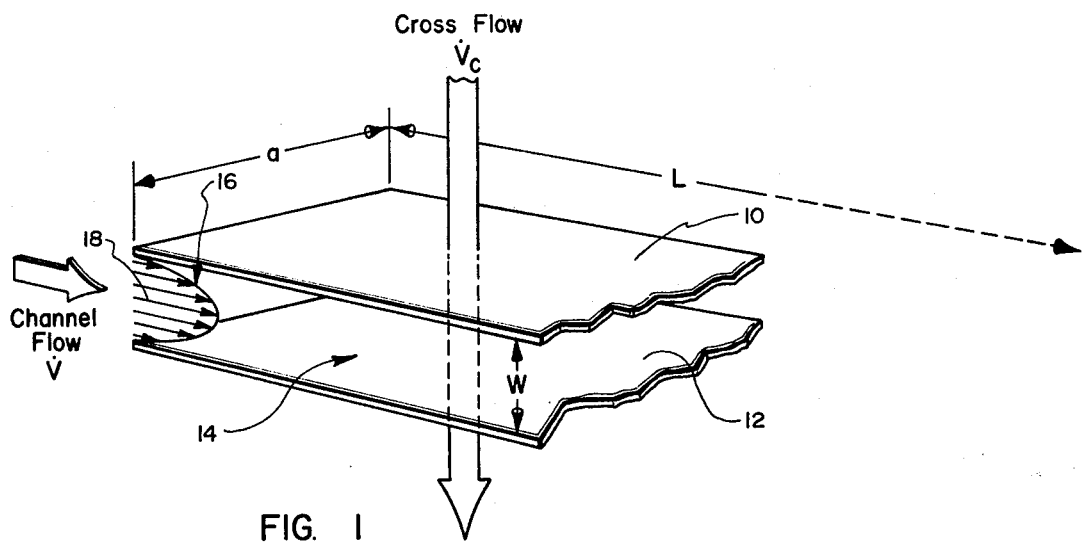
FIG. 1 is a partial cutaway, perspective view of a Flow-FFF channel.

Referring to FIG. 1, the basic concept of Flow-FFF in represented by the flow vectors $\dot{V}$ and $V_c$. These vectors are drawn in relation to two, closely spaced, parallel plate means, 10 and 12. The region between these plates is identified as a flow channel 14, through which a solute/solvent combination is conducted. This fluid flow is represented by a channel profile 16 which shows relative fluid movement by means of channel flow vectors 18. Therefore, the average channel flow is represented by a single flow vector $\dot{V}$; however, this average value is composed of differing channel flow vectors 18 whose magnitude decreases as the fluid location is more proximate to the respective plate means, 10 and 12.

The theory of Flow-FFF is related to conventional FFF in that a cross field is imposed normal to channel flow for the purpose of causing solute migration therein. This cross flow is illustrated as $\dot{V}_c$ oriented perpendicular to the channel flow $\dot{V}$ and the respective plate means.

Whereas with external force fields, the responsiveness of the solute particles often depended on the existence of unique chemical/physical properties such as electrical charge, density, thermal diffusion, etc., the cross flow influence has universal application to any particle regardless of its unique properties. Since all particles will be subjected to this migrating influence, the only remaining requirement for solute separation by Flow-FFF is for the subject particles to have differing diffusion coefficients (D).

Figure 2:
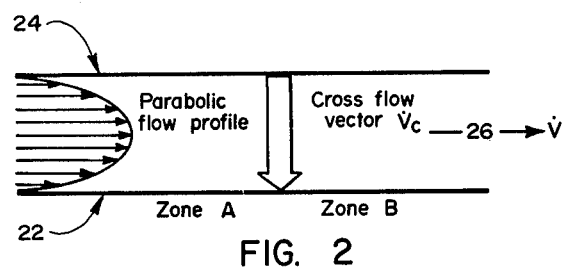
FIG. 2 is a side view of a flow profile within the channel showing differentiation of solute displacement as Zones A and B.

The dynamics of this fluid-flow segregating influence, along with the theoretical basis, is discussed in greater detail in Guddings, Yang and Myers, *Analytical Chemistry*, 48, p 1126 (July 1976). Simply stated, as the different solute particles move down the channel, the cross flow causes the various solute particles to migrate to the slower fluid flow region adjacent to the wall 22 as shown in FIG. 2. When the particles have different diffusion coefficients, the resultant counter movement away from the wall leads the particles to different mean distances from the wall and this to differential flow rates represented by the indicated channel flow vectors. These differential flow rates tend to separate the different solutes contained within the channel.

In FIG. 2, the particles of Zone A are most proximate to wall 22, having been displaced away from wall 24 by the cross fluid flow. Therefore, they move with the slowest rate of channel flow, being most proximate to the indicated wall retarding surface. Likewise, the solute of Zone B is forced near to wall 22; however, this solute has a higher diffusion coefficient and therefore diffuses more strongly back toward the center of the flow channel 26. Because of the increased rate of flow of this inner region, the particles of Zone B tend to segregate down stream of the particles of Zone A. Thus, the desired separation is effected.

The specific structural formulae and derivation of theoretical relationships governing channel dimensions and flow rates are fully developed in the article cited previously. An important relationship disclosed therein is a definition of diffusion coefficient in terms of "a" the channel breadth, "L" channel length, "$\dot{V}_c$," "$V_o$" channel volume (aLw), and "$\lambda$":

$$D = \frac{\lambda \dot{V}_c V_o}{a^2 L^2}$$

$\lambda$ is a dimensionless factor equal to l/w, in which w equals channel width and l equals the characteristic thickness of a steady-state exponential layer of solute particles. This "steady-state" occurs where the lateral solute migration caused by $\dot{V}_c$ is countered by the diffusion (D) in the opposite direction to stabilize the solute to a characteristic exponential layer of approximate mean thickness l.

Although this relationship (1) for diffusion coefficient values is helpful in assigning channel dimension values of a, L and w, the most important factor w can practicably be defined as the smallest separation which can practically be obtained between the plates, 10 and 12. Typically, this value is in the range of several millimeters or less; however, the limitations appear to be more practical than theoretical. Therefore, the final separation for a given channel configuration will probably be based on experimental evaluation of performance with a primary objective of minimizing the value of w.

It is apparent, both intuitively and from relation (1), that increases in the field strength $\dot{V}_c$ will be a primary factor in the degree of separation and upon the retention time ($t_r$) of the solute within the chamber. By controlling $\dot{V}_c$, in combination with $\dot{V}$ (the channel flow rate), the factors of retention time and separation rates can be usefully controlled and applied to numerous separation techniques.

Figure 3:
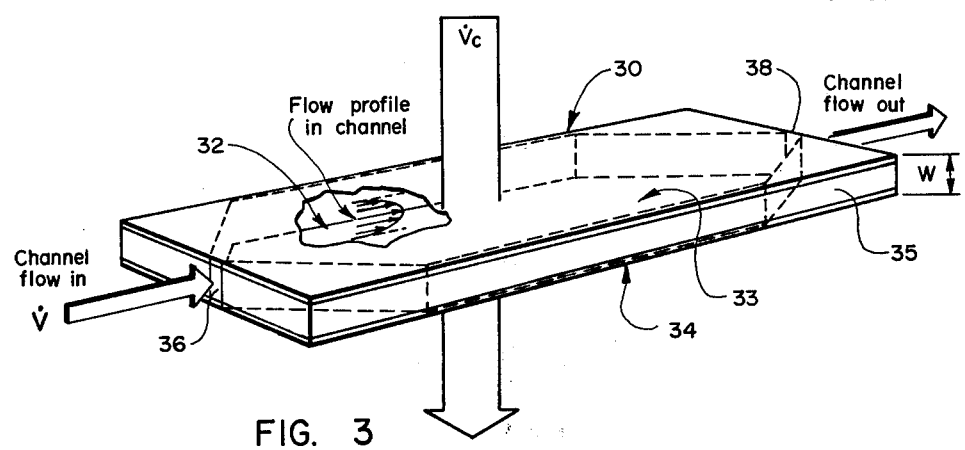
FIG. 3 depicts a Flow-FFF channel with enclosing structure around the channel.

Structurally, the aforementioned theory can be implemented by many variations of basic elements as shown in FIG. 3. The flow channel 32 is substantially defined by a first and second semipermeable plate means, 33 and 34. These plates may be constructed of any suitable material which will permit passage of selected fluids to be used as a cross flow fluid, but must be impermeable to one or more solutes and/or solvent comprising the channel fluid constituents. Numerous membranes are available commercially and are appropriately categorized as to which molecule sizes will diffuse therethrough.

The geometry of these plates is customarily elongated to provide sufficient length to the flow channel to permit full solute segregation and effective operation of the cross flow force. Here again, the actual dimensions will probably be experimentally determined to provide a length sufficient for the intended purpose of the apparatus. The breadth (a) of the chamber can be varied within the practical ability of maintaining uniform fluid flow across the plate 33 surface area.

Side wall structure 35 is affixed to the respective plate means to fully enclose the chamber region 32. Since no flow should occur through the side walls, this must be of nonporous material. A general configuration might comprise a spacer plate 35, having the desired thickness (w), interposed between the respective semipermeable plates, the combination being tightly clamped together.

Inlet means 36 and outlet means 38 are provided at opposite ends of the chamber to enable channel flow therebetween. Control means associated therewith would be desireable to facilitate adjustment of $\dot{V}$. The inlet may be adapted for either continuous or pulse injection methods. Typically, the outlet will feed effluent to detection means for obtaining separation results.

Operation of the apparatus begins with the filling of the channel either through the channel inlet or first plate means. Channel flow is then effected along a channel axis extending the length of the channel region. The cross flow is applied by establishing a desired rate of entry fluid flow through the first semipermeable plate means perpendicular to the channel axis. Exit fluid flow occurs at the second plate means by virtue of the limited exit capability of the outlet means.

With the control valves for channel and cross flow appropriately regulated, the solute containing fluid is then introduced in the channel fluid flow line.

Figure 4:
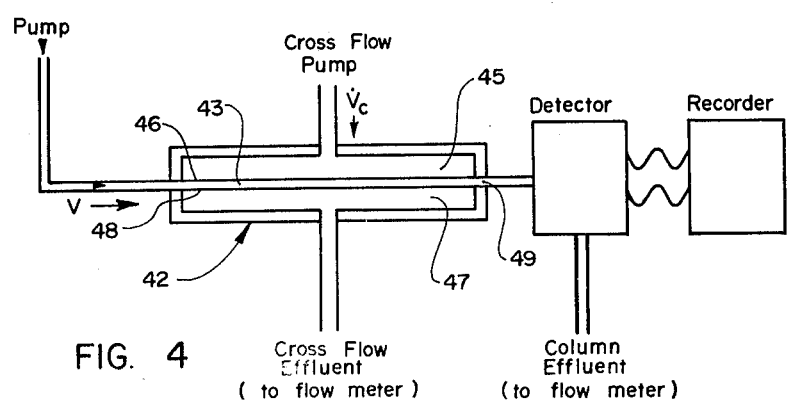
FIG. 4 is a block diagram of a Flow-FFF system.

This operation is represented in block diagram in FIG. 4. As represented, channel fluid is pumped through the narrow channel 43 of the general apparatus 42. The desired cross flow is obtained by maintaining fluid pressure at a predetermined level within an upper solvent chamber 45, or by a positive displacement pump. This fluid pressure is thereby imposed at the semipermeable membrane 46, which results in fluid passage into the channel and subsequently, fluid flow into the lower solvent chamber 47 through membrane 48.

As indicated in FIG. 4, fluid exits the apparatus from the channel outlet 49 and a cross-flow effluent outlet. Since regulation of fluid flow is desirable, both outlets are fed to flow meters for registering flow rates. In the case of channel effluent, its fluid path passes through a detector for analysis of solute separation. A recorder is provided for analyzing and/or recording data.

As will be apparent from specific applications of the subject apparatus discussed hereinafter, FIG. 4 represents only one of many Flow-FFF embodiments. With different uses, for example, a detector means may be located in the cross flow effluent path either in combination with or as an alternative to the previously referenced detector location. These potential variations will be more apparent with the disclosure of the following examples, which is by no means intended to be exhaustive.

1. Separation/Fractionation Processes

Because of the capability of Flow-FFF to handle very broad ranges of particle sizes, the subject apparatus is well suited for separation processes. Using an apparatus similar to that previously discussed, solute separations were tested in a particle range from polystyrene beads with a mean diameter of 4810 Å to B-casein with a molecular weight of 24,100. This range represents a mass ratio between these extremes of about 1.5 million. Furthermore, this particular range does not represent the limits of particle separation.

Figure 5:
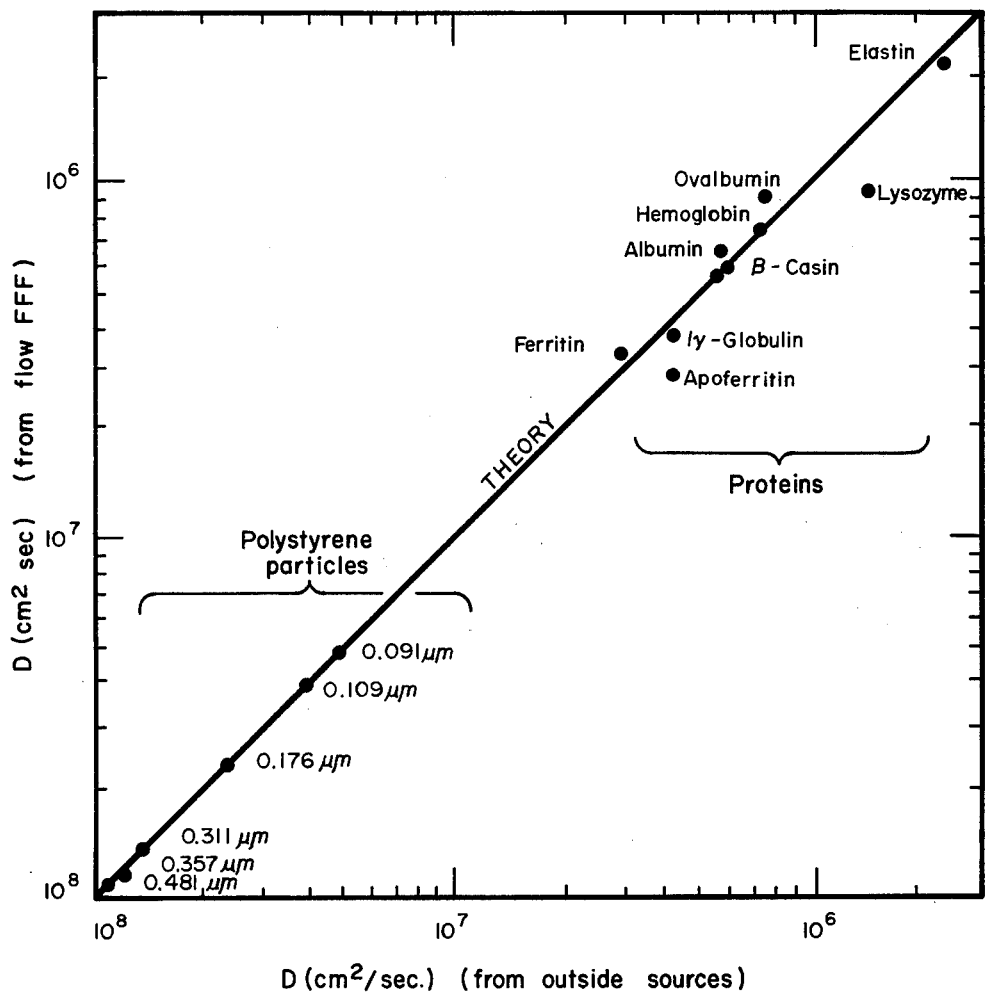
FIG. 5 is a graphical comparison of theoretical and actual experimental results of Flow-FFF application to separation of various indicated types of solute material.

FIG. 5 illustrates the differentiating capability of the subject apparatus, with a 0.25 mm channel thickness, channel flow rates between 3.5 to 6.8 ml/hr and cross flow rates from 6.4 to 24 ml/hr and 24 to 48 ml/hr for latex beads and proteins respectively. The abscissa provides values for diffusion coefficients (D) taken from sources independent of Flow-FFF. The ordinate compares values of D derived from particle retention measurements of a Flow-FFF method via an equation similar to equation (1), supra. The comparison is made on the basis of diffusion coefficients, in that retention in Flow-FFF is predicted to depend on these parameters. The close correlation between these determinations substantiates the separation capability of Flow-FFF.

This technique has also been applied to a solute class of viruses. Here again, the versatility of Flow-FFF was demonstrated as positive retention of various solute components was registered. Specific experimental results are disclosed in Giddings, Yang and Myers, *J. of Virology*, 21, p 131–138 (Jan. 1977).

Other applications of this methodology include a convenient method of separating numerous particle sizes in a single solvent (such as an analysis of drinking water) involving programming cross flow rates. This is accomplished by providing automatic controls for regulating cross flow from an initial high rate of flow to a sequentially lesser flow rate. Under this procedure, larger particles are initially forced against the exit flow semipermeable plate and retained in fixed location. The decreasingly smaller particles, being less subject to the cross-flow force, diffuse more toward the central channel axis flow. These smaller particles therefore migrate downstream of the larger retained particles.

By gradually decreasing the rate of cross flow, the successively larger particles progressively free themselves from retention and are also carried downstream. The overall effect of such programmed flow is to nicely segregate the time of particle emergence in the channel effluent from small to larger sizes. It is also apparent that by presetting the rates of flow, a specific narrow range of particle size separation can be effected.

2. Purification, Ultrafiltration and Dialysis Processes

A continuous solution exchange cell is an additional application of the flow field-flow fractionation device. By means of flow adjustments it can be operated as a pressure dialysis (diafiltration) cell, a dialysis cell, or as an ultrafiltration unit. It has good throughput, low volume, short solute residence times and can be scaled to almost any size and capacity.

Figure 6:
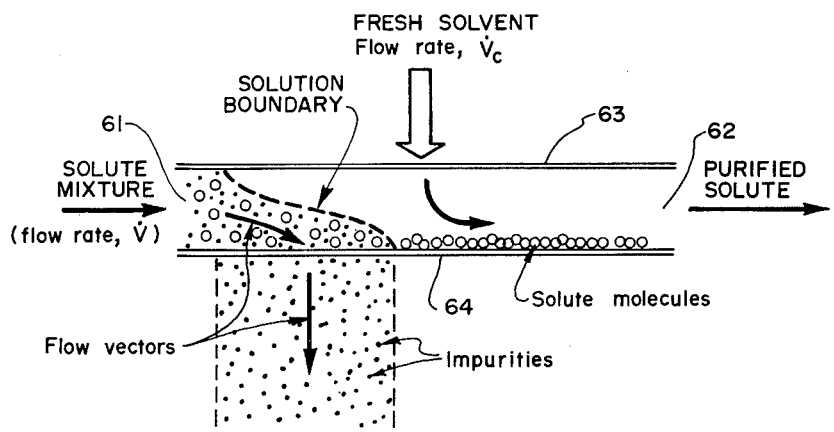
FIG. 6 shows a simulated action diagram for a purification, ultrafiltration dialysis or pressure dialysis mode of operation for the subject invention.

The cell consists of a Flow FFF channel similar to that previously described. The operation of the device is illustrated in FIG. 6. The contaminated solute stream (with first solvent) is fed into inlet 61 of the channel region and the purified solute is collected at the outlet at the opposite end 62. A fresh solution, of whatever composition desired, is forced in through the first semipermeable plate means 63, forcing the original solution (minus the desired solute) out the second semipermeable plate means 64. Since the purpose of this configuration is to retain the solute molecules within the channel, the degree of permeability of the latter plate must be sufficient to let only the first solvent and impurities pass.

Operating in the continuous pressure dialysis of diafiltration mode, the Flow-FFF channel will allow the operator to change in any desired way the final composition and concentration of background solvent or electrolyte. A salt of one concentration can be almost totally exchanged with another salt or organic material of another concentration. Solute concentration can also be varied in any direction if desired (pressure dialysis or ultrafiltration mode). Likewise, solvent exchange can be controlled for any desired purpose.

Control of these variables is a result of the fact that four separate flowrates can be manipulated in such a way as to achieve the desired purposes. These flowrates are those at the inlet 61 and outlet 62 of the channel (axial) flow stream and the entry 63 and exit 64 plates of the crossflow stream, as shown in FIG. 6. Three can be manipulated independently and the fourth is then fixed by the condition that the total inflow and outflow of liquid must be equal.

Small cell volume combined with good throughput leads to short residual times for solute in the FFF cell. The actual scale can clearly be adapted over a wide range, at least from microcells of 10 or so microliters to units capable of processing many liters per hour.

Other types of dialysis and ultrafiltration methods have demonstrated a similar high capacity and, between them, a spectrum of capabilities. The hollow fiber bundle, for example, is particularly high in surface area and throughput, but under normal ultrafiltration conditions, solute is concentrated and impurity removal is incomplete. Many other configurations exist for ultrafiltration units, but each is rather specific and limited in function. The FFF cell avoids these problems and restrictions because the incoming cross flow can be used both to flush the system with the desired background composition and to dilute or concentrate the solute as desired.

As with previous applications of the subject apparatus, certain restraints obviously exist which depend on geometry, type of membrane, degree of purification desired, and so on. These limitations are suggested in FIG. 6, which shows the idealized pattern of fluid movement and of solute and impurity displacement in the flow cell. The fluid at any point is obviously subjected to two flow vectors, a horizontal component from the solute feed solution and a vertical component from the fresh solution entering through the face of the upper plate means. The solution boundary, where fresh solution meets the impure mixture and displaces it downward, lies parallel with a local flow vector at each point. Both the solution boundary and the direction of the local flow vector will bend to the vertical at the membrane interface where horizontal flow ceases.

The most obvious requirement for the successful operation of this system is to proportion the respective channel and cross flows so that the solution boundary is driven into the membrane, rather than being allowed to elute in the (purified) solute stream at 62. This simply requires that the stream of fresh solution at the first plate means must arrive at the lower membrane before the original mixture with its impurities reaches the end of the channel 62.

The degree to which cross flow should exceed axial (channel) flow depends on several factors. First, the solution boundary is diffuse rather than sharp, due to the interdiffusion of components. Thus, at equal flows of the cross and axial streams, impurities that have diffused into the fresh solution will be eluted with the desired solute. A greater cross flow is needed to sweep this diffuse boundary down through the lower membrane. The required increase in vertical flow depends on the purity desired, and upon relative flow and diffusion rates.

Upon first consideration, it appears that there is no limit to throughput in the FFF cell if one simply keeps increasing the cross and axial flows in proportion. However, as with any semipermeable membrane method, concentration, polarization and other transport processes limit the rate of purification. With increasing cross flow, the solute is compressed to an increasing degree against the lower membrane. This increases the resistance to cross flow and the back pressure. It may also encourage precipitation and solute leakage through the membrane.

Also, with increasing compression of the solute layer, its mean axial displacement velocity relative to that of the solvent decreases because solute resides increasingly in the almost stagnant flow region next to the wall. This is the same phenomenon, acting selectively, which is responsible for separation outlined in the previous discussion. The resultant lower relative velocity means that more solute must pile up in any given region to maintain steady-state throughput.

In the ideal case, then, a doubling of both flow velocities will double throughput, but it will quadruple the solute concentration at the lower membrane. It will double once because of layer compression, and once more because of the solute buildup caused by relative velocity retardation and increased throughput. The actual (nonideal) case will reflect these general trends. Experimentally, then, there will be a finite limit to throughput for any given cell.

Optimization of throughput is further enhanced by reducing the thickness which separates the respective plate means, by increasing the length of the channel (enabling increased flow rates), and by otherwise increasing surface area of the semipermeable plate means. Simply stated, improved performance is accomplished with maximum plate area and minimum thickness.

The subject purification/dialysis capability has been confirmed in an Flow-FFF cell of construction similar to that of separation type Flow-FFF apparatus. The cell dimensions were 42.2×1.65×0.038 cm, giving a volume of 2.65 ml. Rigid membrane channel walls were constructed by casting cellulose acetate membranes on two rigid, porous polypropylene plates. The membranes were tested and confirmed for 100% retention of small protein molecules such as albumin before the following studies were made.

Methylene blue (MW 320) was chosen as the indicator to demonstrate the removal of small molecules such as salt ions and organic solvents from macromolecules in the cell. An acetate buffer solution (0.2 M sodium acetate adjusted to pH 5.4 with acetic acid) containing $6.1 \times 10^{-5}$ M methylene blue was fed into the inlet end of the dialysis cell by a metering pump (Laboratory Data Control) at a flow rate of about 5.6 ml/hr. A Nupro needle valve placed at the outlet was used to maintain a constant axial flow rate. The cross flow stream, consisting of pure acetate buffer was provided by a separate pump. The cross flow was changed stepwise from about 5 to 100 ml/hr. After each change of cross flow rate, a time of two hours was allowed to re-establish steady conditions. The volumetric flow rates of both axial and cross flow streams were then measured. The concentration of methylene blue in the exit stream was derived from its absorbance relative to that of pure acetate buffer at a wavelength of 600 nm.

In order to determine the effect of high protein concentration on the rate of dialysis, 100 g of bovine serum protein (Miles Laboratories) was added to 1 liter of the methylene blue-acetate buffer solution described above. The resulting solution was then fed into the cell. By following the same procedure as before, the concentration of methylene blue in the stream exiting from the dialysis cell was measured. The absorbance due to albumin was subtracted out from the total absorbance measured. The axial flow rate in this study was 18 ml/hr.

The capability of the cross flow in purging methylene blue from the channel stream is illustrated in FIG. 7. The percentage removal is calculated from the measured concentrations of methylene blue in the channel feed stream ($c_o$) and channel outlet stream (c). The figure shows this percentage to rise steadily with the increased ratio of cross flow to channel flow. This result is expected because the flow ratio indicates the number of times that the incoming solution is effectively removed and replaced by fresh solution during passage of the solute through the channel.

The near coincidence of the two sets of data in FIG. 7 demonstrates that the percentage removal is not seriously affected by the presence of albumin in solution under the experimental conditions. Also, the percentage removal does not seem to be reduced by overall flow rate increases under these conditions in that the axial flow rate was more than three times larger (18 ml/hr versus 5.6 ml/hr) with the protein solution than with the reference solution.

The ability of the Flow-FFF cell to operate as a medical dialyzing apparatus is inherent in the results of the previous experiment. The cell could be placed in series with conventional hemodialysis or peritoneal dialysis systems and operate to cleanse impurities from the treated fluid. A primary advantage of this type of dialysis cell is the control available by regulating channel and cross flow rates.

3. Determination of Diffusion Coefficients

An additional utility inherent in the Flow-FFF apparatus is the ability to experimentally define values of D—diffusion coefficient. Referring again to equation (1)

$$D = \frac{\lambda \dot{V}_c V_o}{a^2 L^2}$$

the members of the right side of this expression can all be measured or otherwise derived by experimental results obtained from the subject apparatus. Calculation of D therefore is elementary, using this or similar expressions of Flow-FFF parameters.

The various embodiments illustrated in the figures are shown as planar-plate configurations for simplicity of illustration. It will be recognized that other nonplanar structures can be constructed utilizing the concepts disclosed herein. Furthermore, although preferred forms of the our invention have been herein described, it is to be understood that the present disclosure is by way of example and that variations are possible without departing from the scope of the hereinafter claimed subject matter, which subject matter we regard as our invention.

We claim:

1. A flow field-flow fractionation apparatus, including:
    (a) elongated first and second semipermeable plates substantially parallel in orientation and closely spaced apart to form a partially bounded, narrow, elongate channel therebetween, said first plate being adapted for entry fluid flow therethrough to said channel and said second plate being adapted for exit fluid flow therethrough, thereby establishing a cross-flow fluid path through said elongate channel, said semipermeable plates being permeable to said cross-flow fluid but impermeable to at least one constituent of a channel fluid which flows along an axis defined by said channel;
    (b) nonporous side walls laterally circumscribing said elongate channel and affixed in combination with said first and second plates to define lateral bounds of said elongate channel;
    (c) inlet and outlet means located at respective ends of said elongate channel for permitting flow of channel fluid along said axis; and
    (d) crossflow fluid control means in association with said plates for controlling and regulating rate of crossflow;
the combination being adapted for use with said respective channel and crossflow fluids to establish a crossflow pressure gradient as an influencing force for laterally displacing substances carried in said channel flow toward said second semipermeable plate.

2. Apparatus as defined in claim 1, wherein said semipermeable plate comprises a semipermeable membrane affixed to a rigid support plate of porous character.

3. Apparatus as defined in claim 1, wherein said side wall comprises a nonporous spacer plate having a thickness equal to a desired channel thickness and having a void central portion which, when clamped between said first and second plate means, forms said narrow channel.

4. Apparatus as defined in claim 1 further comprising regulating valves and pumps in combination with said inlet and outlet means to enable control of flow rates along said channel axis.

5. Apparatus as defined in claim 1, wherein said crossflow fluid control means includes a variable, flow regulating means for automatically changing flow rates in accordance with a predetermined flow rate sequence.

6. Apparatus as defined in claim 1, further comprising channel flow regulating means for automatically changing flow rates in accordance with a predetermined flow rate sequence.

7. A method of establishing a crossflow across a field-flow fractionation channel having elongated first and second plates substantially defining a narrow flow channel therebetween, said method comprising the steps of:
    (a) selecting a semipermeable material suitable for passage of a crossflow fluid therethrough,
    (b) adapting said semipermeable material with rigid structure to enable use thereof as a semipermeable plate in a field-flow fractionation system,
    (c) constructing a flow field-flow fractionation channel using said semipermeable plates as first and second plates, and
    (d) applying a regulated rate of fluid cross flow at said first plate means, in combination with a channel fluid flow, to establish a cross-flow, substantially perpendicular to said channel flow.

8. A method as defined in claim 7, wherein said flow field-flow fractionation is applied as part of a separation technique for separating different particles within a channel fluid comprising a first solvent for carrying said particles within said channel, said channel fluid being subjected to fluid cross-flow of a second solvent at a sufficient flow rate to cause differential particle migration along the axis of channel flow.

9. A method as defined in claim 7, wherein said flow field-flow fractionation is applied as part of a solute purification technique to separate large solute from smaller solute particles by removal of said smaller particles through said second plate, said semipermeable material selection being made within a class of materials impermeable to said larger solute but porous to said smaller solute particles.

10. A method as defined in claim 7, wherein said flow field-flow fractionation is applied as part of a solvent exchange technique, said method comprising the steps of:
    (a) introducing a first solvent containing a solute material into said channel, said second semipermeable plate being permeable to said solvent but nonporous to said solute;
    (b) imposing a cross-flow of a second solvent through said first semipermeable plate; and
    (c) maintaining a sufficient rate of crossflow to cause at least a diffuse solution boundary to arise at an interface of said first and second solvents and to terminate at said second semipermeable plate, thereby precluding elution thereof at a channel outlet.

11. A method as defined in claim 7, wherein said flow field-flow fractionation is applied to a solute exchange technique, said method comprising the steps of:
    (a) introducing a first solvent/solute combination into said channel, said second semipermeable plate being permeable thereto;
    (b) imposing a crossflow of a second solute/solvent combination, said second semipermeable membrane being impermeable to said second solute; and
    (c) maintaining a sufficient rate of crossflow to cause migration of said first solute through said second semipermeable plate, said second solute being retained as part of a channel effluent.

12. A method as defined in claim 7, wherein said steps are adapted to perform a method of application selected from the group consisting of ultrafiltration, pressure dialysis, and purification.

13. A method as defined in claim 7, further comprising the step of placing said flow field-flow fractionation channel within a sterile circuit of a body-fluid dialysis machine, applying said body fluid as channel fluid therein, and imposing a crossflow fluid to cause migration of smaller-size, contaminant matter through said second semipermeable plate, said second plate being operable to retain larger molecules within said channel for return to a body source.

* * * * *